United States Patent [19]

Audibert et al.

[11] 4,220,637

[45] Sep. 2, 1980

[54] WATER SOLUBLE AGENTS EFFECTIVE AS IMMUNOLOGICAL ADJUVANTS FOR STIMULATING IN THE HOST THE IMMUNE RESPONSE TO VARIOUS ANTIGENS AND COMPOSITIONS, NOTABLY VACCINES CONTAINING SAID WATER SOLUBLE AGENTS

[75] Inventors: Francoise Audibert, Neuilly-sur-Seine; Louis Chedid; Jean Choay, both of Paris; Edgar Lederer, Sceaux; Pierre Lefrancier, Bures sur Yvette, all of France

[73] Assignee: Agence Nationale de Valorisation de la Recherche, Neuilly-sur-Seine-Cedex, France

[21] Appl. No.: 815,811

[22] Filed: Jul. 15, 1977

Related U.S. Application Data

[63] Continuation-in-part of Ser. No. 519,991, Oct. 22, 1974.

[30] Foreign Application Priority Data

Jul. 16, 1976 [FR] France .................................. 76 21889

[51] Int. Cl.$^2$ .................... A61K 39/00; C07C 103/52; A61K 37/00
[52] U.S. Cl. .............................. 424/88; 260/112.5 R; 424/177
[58] Field of Search ................................. 424/88, 177; 260/112.5 R

[56] References Cited

U.S. PATENT DOCUMENTS

| 4,082,735 | 4/1978 | Jones et al. | 424/88 |
| 4,082,736 | 4/1978 | Jones et al. | 424/88 |

OTHER PUBLICATIONS

F. Ellouz, et al., Biochem. and Biophys. Res. Comm., 59, 1974, pp. 1317-1325.
Ghuysen, et al., Bact. Membranes and Walls, 1973, pp. 39-41.
Chaturvedi, J. Med. Chem., 9, 1966, pp. 971-973.
Kotani, et al., Sympos. Internat. on Bact. Immun. Stimulants, 1973, p. 8.
Lamzelotti, et al., J. Am. Chem. Soc., 86, 1964.
Kotani, et al., Biken J., 13, 105–111, 1975.
Adam, et al., Biochem. and Biophys. Res. Commun., 72, 1976, pp. 339–346.
Chem. Abst., 87, 1977, pp. 199018m, 118075c, 51519e.

*Primary Examiner*—Delbert R. Phillips
*Attorney, Agent, or Firm*—Weiser, Stapler & Spivak

[57] ABSTRACT

The invention relates more particularly to the diamide of the 2-(2-acetamido-2-deoxy-3-O-D-glucopyranosyl)-D-propionyl-L-alanyl-D-glutamic acid, to the pharmaceutical compositions containing said compound in association with a pharmaceutical vehicle. Of particular interest are the oil-free compositions containing said compound, particularly the oil-free aqueous sterile isotonic injectable solutions. These compositions are useful as adjuvants for enhancing the immune response to vaccinant antigens, particularly weak immunogens.

20 Claims, No Drawings

WATER SOLUBLE AGENTS EFFECTIVE AS IMMUNOLOGICAL ADJUVANTS FOR STIMULATING IN THE HOST THE IMMUNE RESPONSE TO VARIOUS ANTIGENS AND COMPOSITIONS, NOTABLY VACCINES CONTAINING SAID WATER SOLUBLE AGENTS

This is a continuation in part of application Ser. No. 519,991 filed on Oct. 22nd 1974.

This invention is more particularly concerned with a hydrosoluble adjuvant agent capable of enhancing in a non specific manner the immune response to antigens of a host, which adjuvant agent is formed of the diamide of the 2-(2-acetamido-2-deoxy-3-O-D-glucopyranosyl)-D-propionyl-L-alanyl-D-glutamic acid having the formula

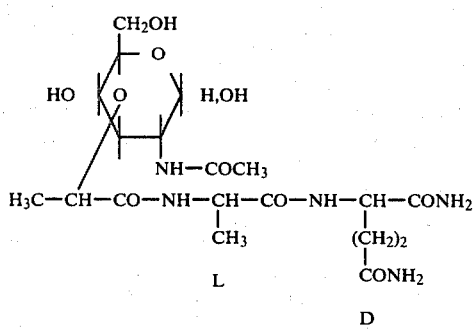

This compound will hereafter be referred to under the abbreviation Mur-NAc-L-Ala-D-Glu(NH$_2$)—NH$_2$.

The invention is more particularly concerned with the adjuvant active oil-free compositions comprising the above said compound associated with a pharmaceutically acceptable carrier. Such compositions are active to reinforce the action of the weak immununogens. The invention is also concerned with a method comprising administering an effective dose of this composition together with a vaccinating antigen in order to protect a host against bacterial, viral and parasital infections, as well as against different tissular antigens of normal or pathological origin.

None of the components other than the active compound in said compositions are necessary for enabling the adjuvant activity of the whole composition to take place when administered to the host together with an immunogen. Obviously compositions containing also an oily phase can also be used in order to take advantage of the adjuvant properties of said compound.

The adjuvant agent or composition can be administered by the parenteral route, such as by injection, scarification, by the oral route or can be applied directly to mucous membranes. It can also be associated with pharmaceutical excipients enabling its administration by the rectal route.

Preferred compositions are the oil-free compositions formed of injectable aqueous solutions containing an effective dose of the product according to the invention. Advantageously recourse can be had to sterile solutions of the compound in an aqueous, preferably isotonic aqueous medium, particularly a glucosed or saline isotonic solution. Obviously these are but examples of preferred compositions without limitative intent. The compound may also be used in the form of a simple solution in distilled water. It may also be used within injectable media containing an oily phase. A suitable composition of this type is disclosed for instance in U.S. patent application No. 656,738 filed on Feb. 9, 1976.

The composition according to the invention may be presented under various forms for the oral route. It can be in the form of a drinkable solution or solid pharmaceutically acceptable composition. Aerosols or gels are suitable for the application on mucous membranes.

The invention also contemplates the lyophilized compound for extemporaneous use, for instance for the extemporaneous preparation of aqueous compositions capable of being administered by sub-cutaneous, intradermic or intramuscular injections, or also by scarification.

Advantageously, the injectable aqueous solutions comprise from about 25 to 100 mg, preferably about 50 mg of the adjuvant compound per dosage unit, associated with a ballast-forming compound, for instance lactose.

The invention also relates to the above said pharamceutical compositions which, in addition contain a vaccinant antigen, particularly a weak immunogen.

The compound under discussion is also useful as a laboratory reactant. It can be used as a standard adjuvant compound for the study of the degree of amplification of the immune responses to antigens of which the immunogenicity is studied, particularly when the latter is weak, or as an antagonist of the immunosuppressive action of compounds known or suspected to have such property in standard biological tests.

Other features of the invention will appear as the description of the preparation and pharmacological properties of the compound under study proceeds.

An example of synthesis of the Mur-NAc-L-Ala-D-Glu(NH$_2$)—NH$_2$ is described hereafter. First, the peptidic chain is prepared. Then this chain is fixed to a muramyl residue. The function of the peptidic chain and of the muramyl residue which do not participate to the reaction are protected by protection or blocking groups which are removed thereafter.

The following abbreviations will be used:
Mur-NAc: 2-acetamido-2-deoxy-3-O-(D-2-propionyl)-D-glucopyranose
Ala: alanine
Glu: glutamic acid
BOC: t-butyloxycarbonyl
OBzl: benzylic ester (a) BOC-L-Ala-D-Glu(NH$_2$)—NH$_2$ (A)

817 mg (2 m moles) of BOC-L-Ala-D-Glu(OBzl)-NH$_2$ obtained according to the method disclosed by P. LEFRANCIER and E. BRICAS (Bull. Soc. Chim. Biol., 1967, 49, 1257), were treated for a period of 48 hours, at ambient temperature, by an ammonia-saturated methanol solution. The reaction mixture was then concentrated and the product obtained crystallized in a methanol-ether mixture. 628 mg of BOC-L-Ala-D-Glu(NH$_2$)—NH$_2$, were obtained, thus with a yield of 97.8%.

M.P.: 108°–112° C.

rotatory power: $[\alpha]_D^{25} = -15°$ (methanol).

The elementary analysis of the compound was as follows:

| C$_{13}$H$_{24}$O$_5$N$_4$ (316.35) | C | H | N |
|---|---|---|---|
| calculated | 49.35 | 7.64 | 17.71 |

-continued

| $C_{13}H_{24}O_5N_4$ (316.35) | C | H | N |
|---|---|---|---|
| found | 49.16 | 7.59 | 17.28 |

(b)
2-(benzyl-2-acetamido-4.6-benzylidene-2-deoxy-3-O-β-D-glucopyranosyl)-D-propionyl-L-alanyl-D-glutamic diamide (B)

633 mg (2 m moles) of (A) were treated with 6 ml of a normal solution of hydrochloric acid in glacial acetic acid. 30 minutes thereupon, the reaction mixture was concentrated to dryness. The oil obtained was taken up into 10 ml of dimethyl formamide containing 0.22 ml (2 m moles) of N-methylmorpholin. A solution in 10 ml of dimethylformamide of 943 mg (2 m moles) of benzyl-2-acetamido-4.6-benzylidene-3-O-(D-carboxyethyl)-2-deoxy-β-D-glucopyranoside, obtained by the method described by R. W. JEANLOZ, E. WALKER, P. SINA (Carbohyd. Res., 1968,6, 184), 0.22 ml (2 m moles) of N-methylmorpholin and 0.26 ml (2 m moles) of isobutylchloroformate was added to the first solution at a temperature of $-15°$ C. The reaction mixture was stirred for 4 hours at $-15°$ C. and 3.4 ml of a 2.5 M $KHCO_3$ solution were added at the same temperature. After 30 minutes, the product was precipitated by adding 500 ml of distilled water. The product was recovered by filtration, washed with water and dried. 1.14 g of the product (B) was obtained with a yield of 89.3%.

The product so obtained was practically pure and was ready for use without further purification.

(c)
2-(2-acetamido-2-deoxy-3-O-D-glucopyranose)-D-propionyl-L-alanyl-D-glutamic diamide (C)

300 mg (0.4 m moles) of (B) were subjected to hydrogenation within glacial acetic acid in the presence of palladium (5%) on carbon, during 10 hours. After filtration, the reaction mixture was concentrated and dried. The residue was dissolved in 5 ml of a 0.002 N acetic acid solution and was eluted on a column of an ion exchange resin, commercialized under the designation AGIX2 by the Company BIORAD, in its acetate form, by means of a 0.02 N acetic acid solution. The fractions containing the compounds of interest were pooled and concentrated. The product was precipitated in a methanol-aceton-ether mixture. 100 mg of Mur-NAc-L-Ala-D-Glu-$(NH_2)$—$NH_2$, were recovered, thus with a yield of 50%. Its rotatory power was of $[\alpha]_D^{25} = +44.9°$ (acetic acid),. Its elemental analysis was as follows:

| $C_{19}H_{33}O_{10}N_5$, 0.5 $CH_3COOH$, 1 $H_2O$ (539.53) | | | |
|---|---|---|---|
| | C | H | N |
| calculated | 44.52 | 6.91 | 12.98 |
| found | 44.45 | 6.95 | 13.02 |

Pharmacological properties of
Mur-NAc-L-Ala-D-Glu$(NH_2)$—$NH_2$

The innocuousness of this product was studied by injecting it intraveneously in two month old mice. Its $DL_{50}$ is far superior to the effective adjuvant doses of this compound.

This compound is fully devoid of any pyrogenic effect, particularly as brought to evidence by the test run on rabbits according to the protocol disclosed in the Pharmacopee Francaise, 9th edition, II-235. Particularly, it was found that at a dose of 2 mg/kg of rabbits to which it was administered sub-cutaneously and intraveneously, the compound according to the invention did not induce any increase of temperature.

The adjuvant effect of the compound according to the invention was brought to evidence under the following conditions.

(a) adjuvant effect in aqueous solution

Groups of 8 two month old Swiss mice were injected subcutaneously with 0.5 mg of the antigen constituted by bovire serum albumin (SAB) and 0.1 mg of the product according to the invention in the form of a saline isotonic solution. The high doses of the antigen induces but a weak or even no response to the antigen in controls owing to the fact that this dose is close to that which inhibits the immune response; the test is accordingly run under most severe conditions as regards the bringing to evidence of the adjuvant activity of the substance studied. Thirty days later, the mice were challenged again with 0.1 mg of the same antigen, yet without adjuvant. The controls were injected with the antigen only, at the first and second times.

The rate of antibodies was determined by passive haemagglutination by resorting to sheep red blood cells which were previously formalin-treated and recovered with the tested antigen according to the technic described by A. A. HIRATA and M. W. BRANDISS (J. Immunol., 100, 641–648, 1968). Blood samples were taken 14,28,34 and 36 days after the first injection.

The results of these tests are indicated in the following table in which the antibody titers correspond to the greatest serum dilution which is capable of agglutinating the SAB-sensitized sheep red-blood cells.

TABLE I

| | titer of antibodies | | | |
|---|---|---|---|---|
| | Primary response | | secondary response | |
| Composition tested | J 14 | J 28 | J 34 | J 37 |
| 0.5 of SAB (controls) | <3 | <3 | <3 | 12 |
| 0.5 mg SAB + 100 μg Mur-NAC-L-Ala-D-Glu $(NH_2)$-$NH_2$ | 6 | 6 | 100 | 300 |

The results thus show that Mur-NAc-L-Ala-D-Glu$(NH_2)$—$NH_2$ is capable, when administered in the form of a saline solution, of inducing an important increase of the rate of antibodies formed.

The compound of this invention is of particular interest owing to its lack of pyrogenicity even at high doses, thereby making it useful for activating the immunological effect of vaccines in human and veterinary therapy.

Thus, oil-free adjuvant compositions are obtained which are deprived of toxicity or noxious secondary effects and therefore particularly suitable for therapeutical applications.

These adjuvant compositions may be used to increase the efficiency of vaccines of bacterial or viral origin, more particularly of those which are weak immunogens. More especially they may be used to increase the host immunity (either human or animal) against infections of bacterial or viral origin, tumor antigens, protozoa antigens, etc.

They are also useful for making serums containing active antibodies against specific antigens.

We claim:

1. The diamide of the 2-(2-acetamido-2-deoxy-3-O-D-glucopyranosyl)-D-propionyl-L-alanyl-D-glutamic acid of the following formula (I):

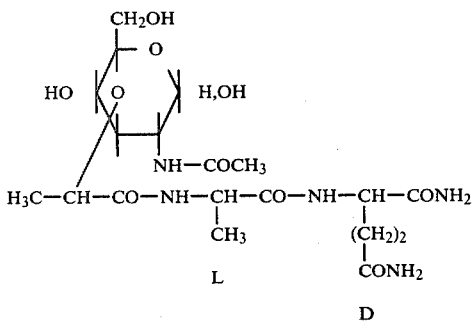

2. An adjuvant-active pharmaceutical composition which comprises in an effective amount, the diamide of claim 1 in association with a pharmaceutically acceptable carrier.

3. The composition of claim 2 which is oil-free.

4. The composition of claim 3 which is in the form of a saline isotonic aqueous solution.

5. The composition of claim 3, in which the active diamide is associated with a pharmaceutical vehicle suitable for the oral administration of said composition.

6. The composition of claim 3 in which the active diamide is associated with a vehicle suitable for rendering said composition directly applicable to mucous membranes.

7. The composition of claim 2 wherein the diamide is associated with a water-oil emulsion, the diamide being dissolved in the water-phase.

8. The composition of claim 2 which further comprises a vaccinant antigen.

9. The composition of claim 3 which further comprises a vaccinant antigen.

10. The diamide of claim 1 which is lyophilized.

11. The lyophilized association of a diamide of claim 1 with a vaccinant antigen.

12. The composition of claim 2, in dosage unit form comprising from about 25 to about 100 mg of the diamide.

13. The composition of claim 3, in dosage unit form comprising from about 25 to about 100 mg of the diamide.

14. A method for enhancing the immune response of the host to an antigen which comprises administering said antigen together with an effective dose of the diamide of claim 1.

15. The method of claim 14, which comprises administering to the host a dosage from about 25 to about 100 mg of the diamide of the 2-(2-acetamido-2-deoxy-3-O-D-glucopyranosyl)-D-propionyl-L-alanyl-D-glutamic acid of the following formula (I):

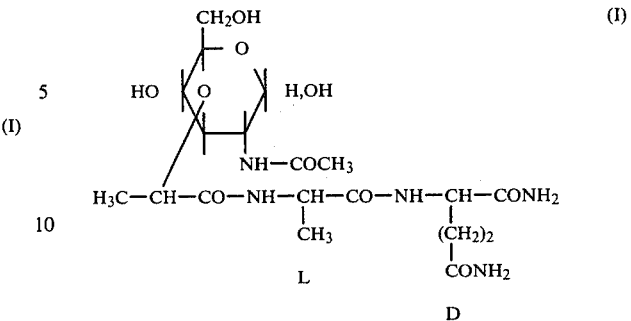

16. The method of claim 14, which comprises administering to the host a dosage from about 50 to about 100 mg of the diamide of the 2-(2-acetamido-2-deoxy-3-O-D-glucopyranosyl)-D-propionyl-L-alanyl-D-glutamic acid of the formula (I):

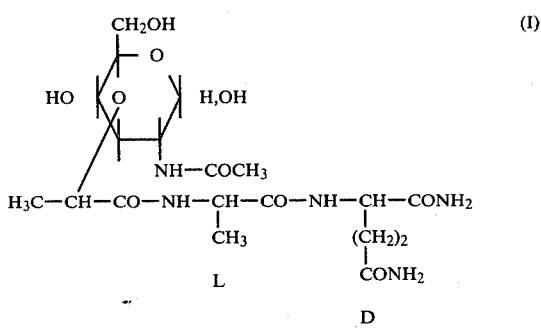

17. The method of claim 14 which comprises administering the diamide of the 2-(2-acetamido-2-deoxy-3-O-D-glucopyranosyl)-D-propionyl-L-alanyl-D-glutamic acid of the formula (I):

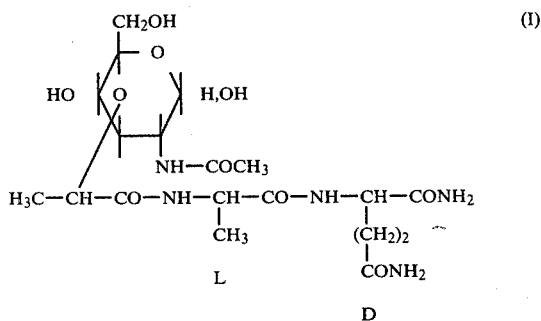

as an oil-free composition containing said diamide.

18. The method of claim 16 which comprises administering said diamide in the form of an aqueous isotonic sterile solution by injection or scarification.

19. A method for enhancing the immune response of a host to an immunogen which comprises administering the composition of claim 2 in an effective dose enhancing the immune response of the host but without pyrogenic effect.

20. The composition of claim 2 which is in a dosage effective to enhance the immune response of a host to an immunogen without causing pyrogenic effect.

* * * * *